(12) United States Patent
Guo et al.

(10) Patent No.: US 12,123,928 B2
(45) Date of Patent: Oct. 22, 2024

(54) VIBRATION GENERATING SYSTEM FOR ELASTOGRAPHY EQUIPMENT AND CONTROL METHOD THEREOF

(71) Applicants: Jing Guo, Berlin (DE); Ingolf Sack, Berlin (DE); Juergen Braun, Berlin (DE); Tassilo Heinze, Döbeln (DE)

(72) Inventors: Jing Guo, Berlin (DE); Ingolf Sack, Berlin (DE); Juergen Braun, Berlin (DE); Tassilo Heinze, Döbeln (DE)

(73) Assignee: THEA-Devices GmbH, Wurzen (DE)

( * ) Notice: Subject to any disclaimer, the term of this patent is extended or adjusted under 35 U.S.C. 154(b) by 488 days.

(21) Appl. No.: 17/438,389

(22) PCT Filed: Mar. 18, 2019

(86) PCT No.: PCT/CN2019/078436
§ 371 (c)(1),
(2) Date: Sep. 10, 2021

(87) PCT Pub. No.: WO2020/181565
PCT Pub. Date: Sep. 17, 2020

(65) Prior Publication Data
US 2022/0187392 A1    Jun. 16, 2022

(30) Foreign Application Priority Data

Mar. 14, 2019  (CN) .......................... 201910192517.8

(51) Int. Cl.
*G01R 33/30*  (2006.01)
*A61B 5/00*   (2006.01)
(Continued)

(52) U.S. Cl.
CPC .......... *G01R 33/307* (2013.01); *A61B 5/0051* (2013.01); *A61B 5/055* (2013.01); *G01R 33/543* (2013.01); *G01R 33/56358* (2013.01)

(58) Field of Classification Search
CPC ....... A61B 5/0051; A61B 5/055; A61B 8/485; A61B 8/5292; A61B 8/54; G01R 33/307; G01R 33/543; G01R 33/56358
See application file for complete search history.

(56) References Cited

U.S. PATENT DOCUMENTS

2013/0296707 A1* 11/2013 Anthony .............. A61B 8/4254
                                                         600/459
2016/0274210 A1   9/2016 Sack et al.
(Continued)

FOREIGN PATENT DOCUMENTS

CN       101632583 A    1/2010
CN       101969845 A    2/2011
(Continued)

OTHER PUBLICATIONS

International Search Report and Written Opinion dated Nov. 27, 2019 issued by the China National Intellectual Property Administration (ISA/CN) in related International Application No. PCT/CN2019/078436; filed Mar. 18, 2019.
(Continued)

*Primary Examiner* — Joseph M Santos Rodriguez
*Assistant Examiner* — Brooke Lyn Klein
(74) *Attorney, Agent, or Firm* — Gordon Rees Scully & Mansukhani, LLP

(57) ABSTRACT

A vibration generating system (100) for elastography equipment and a control method thereof, elastography equipment, a method for controlling the vibration generating system (100) for elastography equipment, a method for operating the elastography equipment, and a corresponding computer-readable medium. The vibration generating system (100) for elastography equipment comprises: a control unit (1), a pressure source (2), a pressure regulating unit (3), and a vibration transmitting unit (4). The pressure regulating unit (3) is in fluidic communication with the pressure source (2)
(Continued)

and the vibration transmitting unit (4), respectively. The vibration transmitting unit (4) is used to transmit vibration according to a pressure acting thereon. The control unit (1) is coupled with the pressure regulating unit (3). The control unit (1) is configured to obtain a control parameter by using a look-up table module (12) according to inputted elastography conditions, so as to control the pressure regulating unit (3).

14 Claims, 6 Drawing Sheets

(51) Int. Cl.
*A61B 5/055* (2006.01)
*G01R 33/54* (2006.01)
*G01R 33/563* (2006.01)

(56) References Cited

U.S. PATENT DOCUMENTS

2017/0086703 A1 3/2017 Wirtz et al.
2017/0332937 A1 11/2017 Kolipaka et al.

FOREIGN PATENT DOCUMENTS

| CN | 202386685 U | 8/2012 |
| CN | 103006216 B | 11/2014 |
| CN | 109419525 A | 3/2019 |

OTHER PUBLICATIONS

European Search Report dated Oct. 24, 2022 issued in related European Patent Application No. 19 919 259.2.

\* cited by examiner

VIBRATION GENERATING SYSTEM FOR ELASTOGRAPHY EQUIPMENT AND CONTROL METHOD THEREOF

TECHNICAL FIELD

The present invention relates to elastography equipment and elastography methods, and in particular to a vibration generating system for elastography equipment and a method for controlling the vibration generating system.

BACKGROUND OF THE INVENTION

It is known that magnetic resonance imaging (MRI) is a medical image acquisition method that uses an external magnetic field to sample and create cross-sectional images of the inside of a body. Except for organs with low water content such as bones, MRI can provide accurate structural images of all other organs and tissues for detecting and evaluating subtle changes in the tissue structure and composition. For example, MRI can effectively present the anatomical structures of soft tissues such as the brain, internal organs, blood vessels, muscles, tendons, ligaments, cartilages, etc. In addition, MRI can also be used to detect changes in brain functions and metabolism, analyze the orientation of tissue fibers, evaluate the main functions, morphology and structure of the cardiovascular system, etc.

Recently, a new imaging technique called magnetic resonance elastography (MRE) based on magnetic resonance imaging has been proposed, which can be used to quantitatively detect the mechanical properties of tissues. For MRE, similar to clinical palpation, external stress needs to be transmitted to the tissue to be examined. Therefore, MRE examines the mechanical properties by detecting changes in tissues under external stress. For this purpose, MRE transmits mechanical vibration to target tissues through, for example, pressure-actuated vibration generating systems. The representations (such as wavelength and amplitude) of the vibration inside a target tissue are recorded in the complex signal of the MRI, thereby forming a dynamic phase images. Based on the phase images, the tissue structure and quantitative mechanical properties can be mathematically reconstructed. By measuring the deformation of the tissue in all spatial directions, MRE can effectively quantify various mechanical properties, such as complex shear modulus, Young's modulus or compression modulus, the spatial anisotropy in the tissue, etc.

During elastography examination, it is necessary to accurately control the vibration generating system. At present, the operator needs to manually adjust the vibration generating system according to the individual differences of the examined objects. However, suitable vibration parameters are affected by many complex and interrelated variables under different elastography conditions. These elastography conditions involve, for example, different organs (different tissue sizes, types, structures, and positions), different pathological states (the same organ has different manifestations in different pathological states), and different body mass indexes (BMI) of the examined objects (difference in vibration penetrability), different vibration frequencies, different motion encoding gradients (magnetic field gradients generated by the gradient coil of magnetic resonance equipment to phase-encode moving objects, in mT/m), etc. Therefore, in order to obtain high-quality MRE data for accurate analysis, the operator needs to have rich practical experience and operation skills. However, this places higher requirements on the operator. In fact, improper operation (such as improper adjustment of the vibration generating system) is an important cause of MRE failure and detection failure.

BRIEF SUMMARY OF THE INVENTION

Therefore, it is desirable to provide a vibration generating system for elastography equipment and a method for controlling the vibrating generation system, which can provide simplified operations, standardized vibration according to elastography conditions, and reduced incorrect equipment parameter settings, thereby improving the accuracy in the elastographic analysis of tissues, and at the same time reduce deviations caused by individual differences of the examined objects.

According to some aspects of the present invention, a vibration generating system for elastography equipment is provided, comprising: a control unit; a pressure source; a pressure regulating unit, and a vibration transmitting unit. The pressure regulating unit is in fluidic communication with the pressure source and the vibration transmitting unit, respectively. The vibration transmitting unit is used to transmit vibration according to a pressure acting thereon. The control unit is coupled with the pressure regulating unit. According to the present invention, the control unit is configured to obtain a control parameter by use of a look-up table module according to inputted elastography conditions, so as to control the pressure regulating unit.

According to some embodiments of the present invention, the pressure regulating unit comprises a pressure excitation valve, and the pressure excitation valve is arranged upstream of the vibration transmitting unit and is in fluidic communication with the vibration transmitting unit. The pressure excitation valve can move between an off position and an operating position, and the frequency of switching between the off position and the operating position can be set by the control unit. In the off position, the vibration transmitting unit is disconnected from the upstream of the pressure excitation valve and is in fluidic communication with the surrounding environment. In the operating position, the pressure from the upstream of the pressure excitation valve is transmitted to the vibration transmitting unit. In this way, through the pressure excitation valve, the pressure acting on the vibration transmitting unit and the vibration frequency can be controlled.

According to some embodiments of the present invention, a waveform generator is also provided, which is coupled with a look-up table module and the pressure excitation valve, and is configured to, based on a control parameter obtained by the look-up table module, generate a waveform signal used for the pressure excitation valve, so as to control the pressure excitation valve.

According to some embodiments of the present invention, the pressure regulating unit further comprises a pressure setting mechanism, and the pressure setting mechanism comprises a pressure setting valve, which is arranged downstream of the pressure source and is in fluidic communication with the pressure source. Preferably, the pressure setting valve is also arranged upstream of the pressure excitation valve and is in fluidic communication with the pressure excitation valve. In this way, through the pressure setting valve, the pressure acting on the vibration transmitting unit can be influenced. For example, when the pressure provided by the pressure source is not suitable for directly acting on the vibration transmitting unit through the pressure excitation valve, the pressure setting valve can be used to adjust and set the pressure upstream of the pressure excitation valve. In addition, when it is necessary to compensate for the amplitude attenuation in the high vibration frequency range that may exist in the MRE technique, the pressure setting valve can be used to adjust and set the pressure with compensation for the upstream of the pressure excitation valve. Preferably, the look-up table module can set the compensation for specific elastography conditions.

According to some embodiments of the present invention, the pressure setting mechanism further comprises a feedback logic unit and a sensor. Preferably, the feedback logic unit is coupled to the pressure setting valve. Preferably, the feedback logic unit is configured to receive a target input used for the pressure setting mechanism and feedback from the sensor. For example, the feedback from the sensor is a parameter sensed by the sensor or corresponds to same in other ways. Preferably, the feedback logic unit is configured to analyze the target input and the feedback (for example, to compare the difference) for feedback control of the pressure setting valve.

According to some embodiments of the present invention, a control module is also provided, which is coupled with a look-up table module and the pressure setting mechanism, and is configured to, based on a control parameter obtained by the look-up table module, generate a target input used for the pressure setting mechanism, so as to control the pressure setting mechanism. Preferably, the target input used for the pressure setting mechanism can be transmitted to the feedback logic unit of the pressure setting mechanism.

According to some embodiments of the present invention, the control module is also configured to perform feedback control, and preferably comprises an integrated feedback logic unit. The integrated feedback logic unit is configured to receive a control parameter and an actual output, and is configured to analyze the control parameter and the actual output (for example, to compare the difference), so as to obtain a regulated target input used for the pressure setting mechanism. The actual output can be feedback from the sensor of the pressure setting mechanism. In this way, the feedback logic unit is configured to receive feedback from the pressure setting mechanism for feedback control. Alternatively or additionally, the actual output may be feedback from an additional sensor. Hence, an additional sensor is also provided. Preferably, the additional sensor is arranged downstream of the pressure setting mechanism. Preferably, the additional sensor is arranged upstream of the pressure excitation valve. In this way, the feedback logic unit is configured to receive feedback from the additional sensor for feedback control. For example, the feedback from the additional sensor is a parameter sensed by the sensor or corresponds to same in other ways.

Although the above description relates to a feedback logic unit that performs analysis and adjustment control, according to other embodiments of the present invention, the execution of analysis and adjustment of control may also be implemented by program modules that implement functions. However, these implementations are only examples and are not intended to limit the present invention.

Preferably, the sensor of the pressure setting mechanism and/or the additional sensor may be a position sensor for sensing the position of the pressure setting valve and/or a pressure sensor for sensing the pressure achieved by the pressure setting valve and/or a flow sensor for sensing the flow passing through the pressure setting valve, and any suitable number of sensors of the pressure setting mechanism and/or additional sensors may be provided.

Advantageously, the proportional-integral-derivative control is used for the feedback control, and in the case of multiple sensors (or multiple types of feedback) in the corresponding feedback loop, a cascade feedback control is used. In addition, the combination of the feedback control of the pressure setting mechanism and the feedback control of the control module is also a form of cascade feedback control. According to some embodiments of the present invention, the pressure regulating unit further comprises a pressure buffer device. Preferably, the pressure buffer device is respectively in fluidic communication with the pressure setting valve and the pressure excitation valve. In this way, the intermittent pressure fluctuations caused by the movement (for example, opening and closing) of the pressure excitation valve can be buffered (relieved).

According to some embodiments of the present invention, the look-up table module stores the correlation between (different) elastography conditions and control parameters used for the pressure regulating unit (preferably, and the pressure parameters and hence the vibration parameters). Preferably, the look-up table module may be comprised in the control unit or the elastography equipment. Preferably, the look-up table module is a look-up table that is stored in a memory and can be accessed. Thus, the correlation is stored in the look-up table and therefore in the memory. Advantageously, the look-up table is editable in order to update the correlation between elastography conditions and control parameters (preferably, and the pressure parameters and hence the vibration parameters) or to add correlation between other elastography conditions and control parameters (preferably, and the pressure parameters and hence the vibration parameters).

According to some embodiments of the present invention, a user control interface is also provided, in order to perform one or more of the following: receiving an input of elastography conditions for use by the control unit; and querying and/or editing the look-up table. Preferably, the user control interface may be comprised in the control unit or the elastography equipment.

According to some embodiments of the present invention, the waveform generator and/or the control module may be part of the control unit. In other words, the waveform generator and/or the control module may be comprised in the control unit. According to some embodiments of the present invention, the waveform generator and/or the control module may be integrated in the pressure regulating unit.

According to some embodiments of the present invention, the elastography conditions include one or more of the following items: organ type, pathological state, BMI, vibration frequency, and motion coding gradient. For example, organs include but are not limited to the brain, heart, and abdominal organs (such as liver, spleen, kidney, and pancreas).

According to other aspects of the present invention, elastography equipment is provided, comprising an image recording device and the vibration generating system according to the present invention.

According to yet some other aspects of the present invention, a method for controlling the vibration generating system of elastography equipment is provided, characterized in that the vibration generating system comprises a control unit, a pressure source, a pressure regulating unit, and a vibration transmitting unit, wherein the pressure regulating unit is in fluidic communication respectively with the pressure source and the vibration transmitting unit, and the method comprises: receiving inputted elastography conditions; using a look-up table module to obtain control parameters used for the pressure regulating unit based on the inputted elastography conditions; using the control parameters to control the pressure regulating unit; and converting, by the vibration transmitting unit, the pressure acting on it into vibration.

According to some embodiments of the present invention, controlling the pressure regulating unit comprises controlling a pressure excitation valve by use of a waveform generator. Preferably, the waveform generator generates a waveform signal for the pressure excitation valve based on a control parameter obtained by the look-up table module. Preferably, controlling the pressure excitation valve comprises controlling the duration, frequency and/or mode (for example, in a square wave, pulse wave, etc.) of the movement of the pressure excitation valve between the off position and the operating position.

According to some embodiments of the present invention, controlling the pressure regulating unit comprises controlling a pressure setting mechanism by use of a control module. Preferably, the control module generates a target input for the pressure setting mechanism based on a control parameter obtained by the look-up table module. Preferably, the pressure setting mechanism performs feedback control in itself. Preferably, the control module receives an actual output from the sensor of the pressure setting mechanism and/or from an additional sensor, and uses the actual output for feedback control.

According to some embodiments of the present invention, the method further comprises using a pressure buffer device for buffering. Preferably, the pressure buffer device is respectively connected to the pressure excitation valve and the pressure setting valve.

According to yet some other aspects of the present invention, a method for operating elastography equipment is provided, comprising: inputting elastography conditions; controlling a vibration generating system by use of the control method according to the present invention; and collecting images by use of an image recording device.

The present invention may also provide a non-transient computer-readable medium storing an entity of a look-up table of the correlation between elastography conditions and control parameters of the vibration generating system, characterized in that, when computer instructions stored in the computer-readable medium or otherwise are executed by a processor, the computer instructions are configured to: receive inputted elastography conditions; access the look-up table to obtain a control parameter based on the inputted elastography conditions; and use the control parameter to control the vibration generating system.

In addition, according to still some other embodiments of the present invention, the vibration generating system may not comprise or use an arrangement similar to the waveform generator and/or pressure excitation valve as described above. However, in some of such embodiments, different arrangements corresponding to a look-up table module may also be used for control. The different arrangements may also comprise the control module, the pressure regulating unit and/or the buffer device and their components according to the present invention individually or in an appropriate combination. According to the present invention, such embodiments can also be controlled and/or operated.

DETAILED DESCRIPTION OF THE EMBODIMENTS

Figure 1:
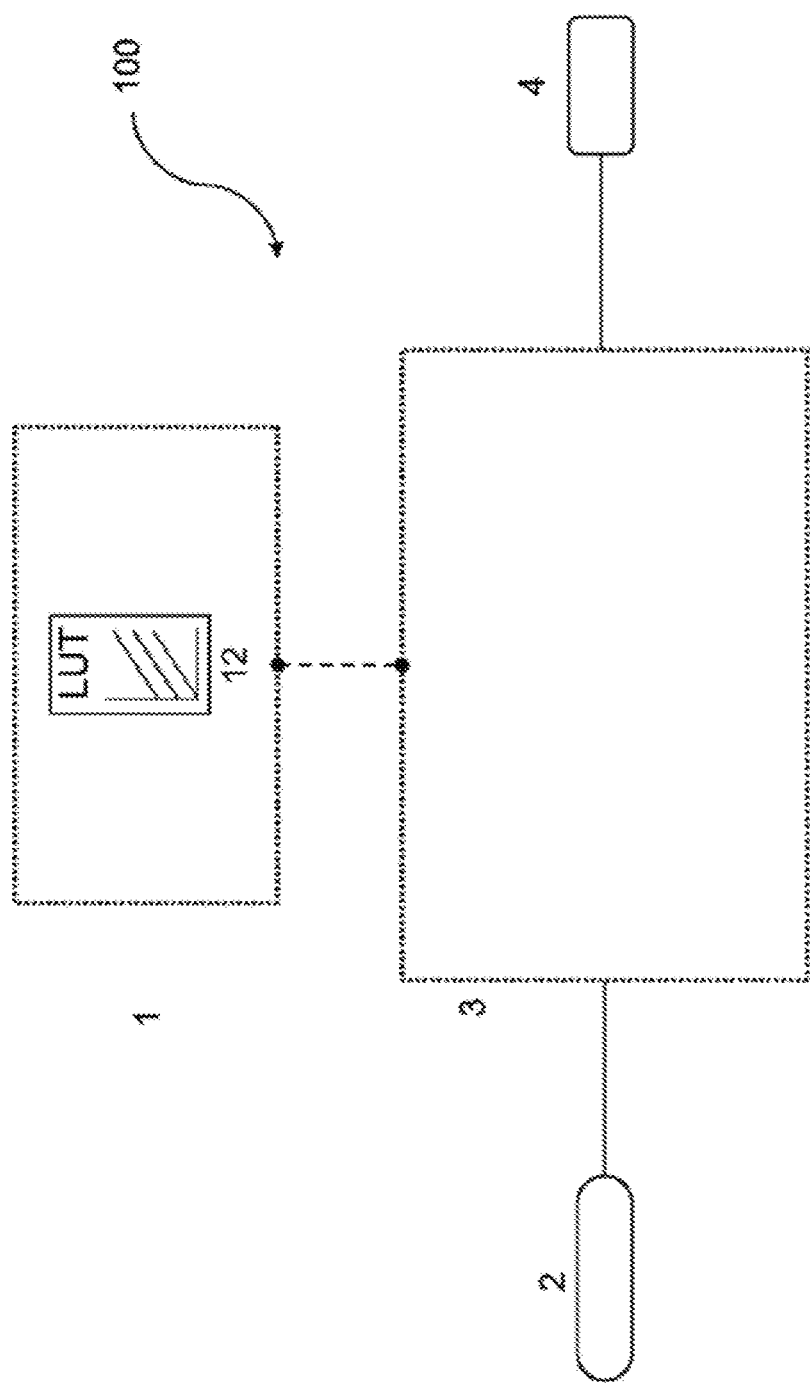
FIG. 1 shows the vibration generating system for elastography equipment according to some embodiments of the present invention.

The present invention will be described with reference to the drawings, which show some embodiments of the present invention. However, the present invention can be implemented in many different forms, and should not be construed as being limited to the embodiments depicted and described herein; on the contrary, these embodiments are provided so that this disclosure will be thorough and complete, and will fully convey the scope of the present invention to those skilled in the art. It will also be understood that the embodiments disclosed herein can be combined in any manner and/or combination to provide many other embodiments.

Unless otherwise defined, all the technical and scientific terms used in this disclosure have the same meaning as commonly understood by those ordinarily skilled in the art to which the present invention belongs. The terms used in the above description are only used for the purpose of describing specific embodiments, and are not intended to limit the present invention.

For ease of description, in the drawings, the same reference numerals refer to the same modules, units, and/or components.

With reference to FIG. 1, FIG. 1 shows the vibration generating system 100 for elastography equipment according to some embodiments of the present invention.

In addition to the vibration generating system 100, the elastography equipment usually also comprises an image recording device. An image recording device is generally commonly known, and therefore it is not described and shown in detail.

According to FIG. 1, the vibration generating system 100 comprises a control unit 1, a pressure source 2, a pressure regulating unit 3, and a vibration transmitting unit 4. The pressure source 2 and the pressure regulating unit 3 are in fluidic communication, and the pressure regulating unit 3 and the vibration transmitting unit 4 are in fluidic communication. The fluidic communication may be implemented by pipeline connections. The control unit 1 and the pressure regulating unit 3 are coupled. For example, the coupling may be done by a wireless or wired connection. Preferably, the control unit 1 and the pressure regulating unit 3 are connected through a multipolar cable. Therefore, although the embodiment in FIG. 1 shows only one connection line coupling the control unit 1 with the pressure regulating unit 3, the present invention is not limited thereto.

As described previously, for different elastography conditions, it is necessary to implement suitable vibration (of different parameters such as the frequency, amplitude and mode of vibration (for example, in a square wave, pulse wave, etc.)). However, suitable vibration is affected by many coupled factors. Here, the vibration depends on the pressure (of parameters such as the magnitude, duration of action, frequency and mode (for example, in a square wave, pulse wave, etc.)) acting on the vibration transmitting unit 4, and the pressure is regulated by the pressure regulating unit 3. The pressure regulating unit 3 is controlled by the control unit 1. In embodiments according to FIG. 1, the control unit 1 comprises a look-up table module 12. The control unit 1 is configured to control the pressure regulating unit 3 by use of the look-up table module 12 based on the elastography conditions, so as to achieve the pressure to be used. Accordingly, the vibration transmitting unit 4 transmits vibration according to the pressure acting thereon.

Preferably, the pressure source 2 comprises a compressed air source. For example, the compressed air source may comprise, without limitation to, an air tank, pipes connected to the compressor, etc. According to some embodiments, the compressed air source provides compressed air at a working pressure of approximately 4-5 bar. In particular, the compressed air at this pressure is beneficial to the operation of the vibration generating system, and is used in common MRI examination rooms. Alternatively, in some other embodiments, the pressure source 2 further comprises a negative pressure source, wherein negative pressure is provided by, for example, a vacuum pump.

Preferably, the vibration transmitting unit 4 comprises a bottle-shaped passive motion unit, which is generally applicable to all the organs of the body.

Figure 2:
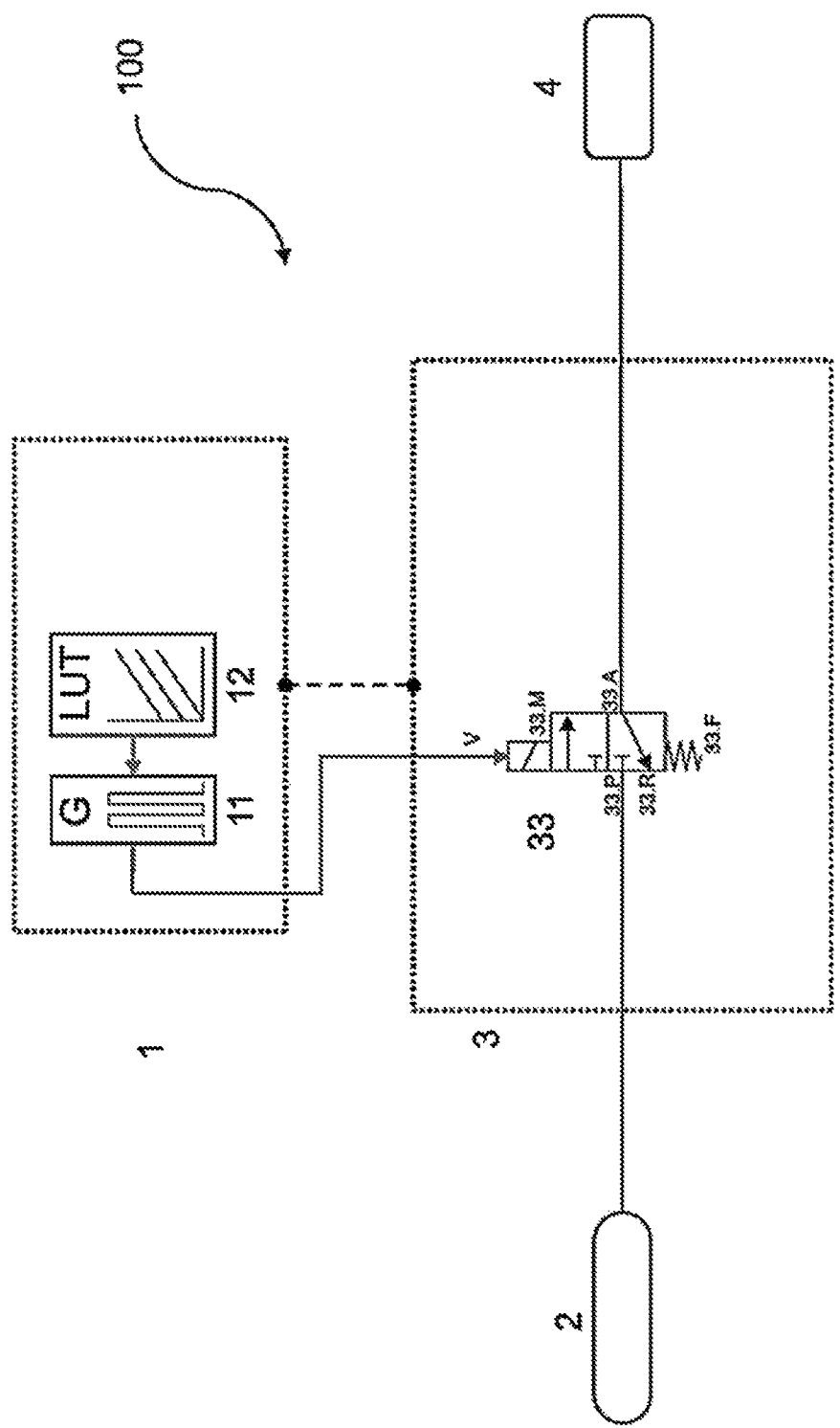
FIG. 2 shows the vibration generating system for elastography equipment according to some other embodiments of the present invention.

With reference to FIG. 2, FIG. 2 shows the vibration generating system 100 for elastography equipment according to some other embodiments of the present invention. The embodiments of FIG. 2 are similar to those of FIG. 1.

As shown in FIG. 2, the pressure regulating unit 3 comprises a pressure excitation valve 33. The pressure excitation valve 33 is arranged upstream of the vibration transmitting unit 4 and is in fluidic communication with it, and is configured to move at different durations, frequencies and/or modes (for example, in a square wave, pulse wave, etc.) between the off position and the operating position according to the control. In the off position, the vibration transmitting unit is disconnected from the upstream of the pressure excitation valve and is in fluidic communication with the surrounding environment. In the operating position, the pressure from the upstream of the pressure excitation valve is transmitted to the vibration transmitting unit. In other words, according to the control, the pressure acting on the vibration transmitting unit is influenced by the pressure excitation valve and changes with time.

Preferably, the pressure excitation valve 33 is a 3/2 solenoid valve. Hence, the valve position (i.e., the operating position or the off position) of the pressure excitation valve 33 can be conveniently controlled. The solenoid valve comprises: an inlet 33.P, which is in fluidic communication with the upstream of the pressure excitation valve; an outlet 33.A, which is in fluidic communication with the vibration transmitting unit 4; a vent 33.R, which is in fluidic communication with the surrounding environment; a return spring 33.F, which is configured to press the pressure excitation valve 33 toward the off position; and an actuator 33.M, which has, for example, windings, and is configured to be powered on and off to move the valve position of the pressure excitation valve. In the off position, the outlet 33.A is in fluidic communication with the inlet 33.P and disconnected from the vent 33.R, whereas in the operating position, the outlet 33.A is in fluidic communication with the vent 33.R and disconnected from the inlet 33.P.

Preferably, the solenoid valve provides a switching frequency of 1-100 Hz. In this way, the risk of cut-off is prevented, and it can operate stably at a relatively high operating frequency (for example, 60-80 Hz).

In order to actuate the pressure excitation valve 33 in the pressure regulating unit 3 according to the control, a control signal from the control unit 1 needs to be applied to the pressure excitation valve 33, for example, to the control port of the pressure excitation valve 33. For this, the control unit 1 comprises a waveform generator 11. The waveform generator 11 is coupled with the look-up table module and the pressure excitation valve 33, and is configured to, based on a control parameter obtained by the look-up table module 12, generate a waveform signal v as the control signal for controlling the pressure excitation valve 33. As needed, the waveform signal v may have different durations, frequencies, amplitudes and/or modes (for example, in a square wave, pulse wave, etc.). Hence, the control parameters used may involve the duration parameter, frequency parameter, amplitude parameter, and/or mode parameter coupled to the waveform generator 11. The waveform signal v will limit the valve position that the pressure excitation valve 33 is in. As a result, the duration, frequency and/or mode of the movement of the pressure excitation valve between the off position and the operating position are controlled, in particular depending on the waveform signal v.

Figure 3:
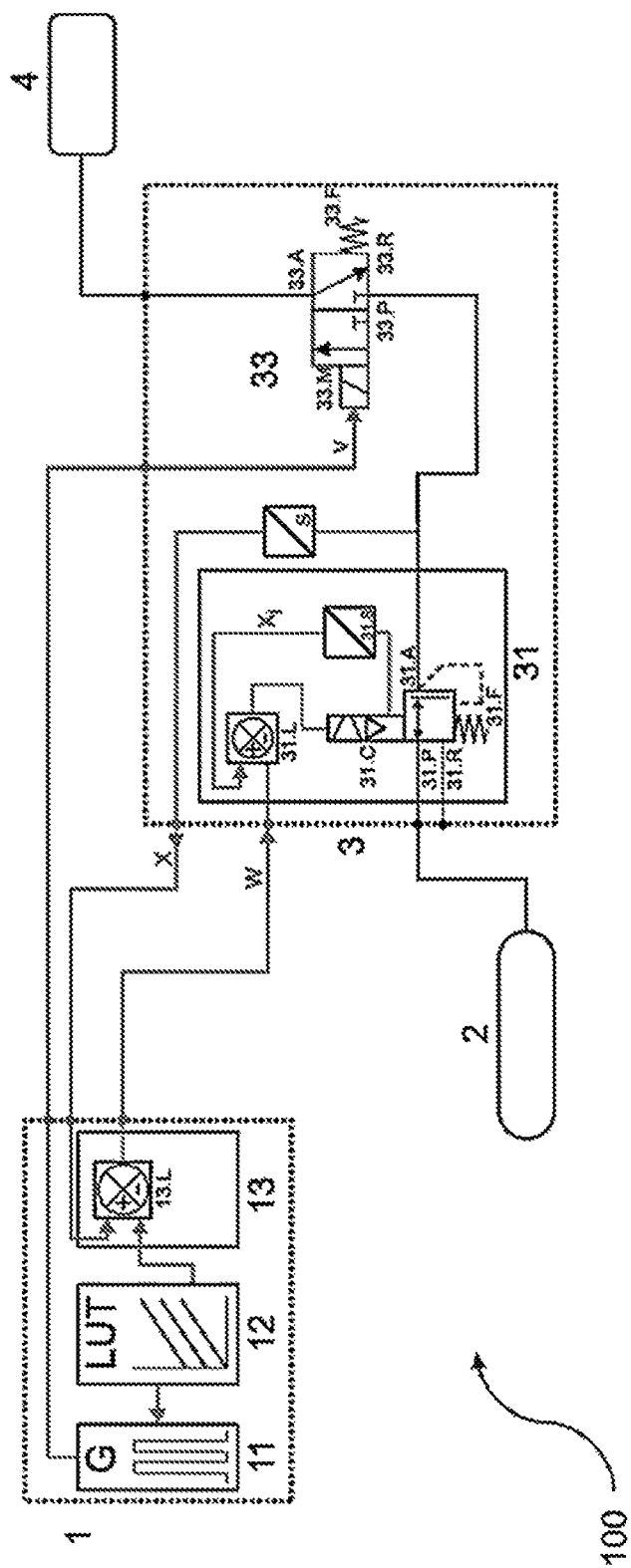
FIG. 3 shows the vibration generating system for elastography equipment according to yet some other embodiments of the present invention.

With reference to FIG. 3, FIG. 3 shows the vibration generating system 100 for elastography equipment according to yet some other embodiments of the present invention. The embodiments of FIG. 3 are similar to those of FIGS. 1 and 2.

As shown in FIG. 3, in addition to the pressure excitation valve 33, the pressure regulating unit 3 further comprises a pressure setting mechanism 31. The pressure setting mechanism 31 comprises a feedback logic unit 31.L, a pressure setting valve 31.C and a sensor 31.s. Advantageously, these components are located inside the pressure setting mechanism 31. Preferably, the pressure setting valve 31.C is arranged downstream of the pressure source 2 and upstream of the pressure excitation valve 33, and is in fluidic communication with the pressure source 2 and the pressure excitation valve 33. By use of the pressure setting valve 31.C, the pressure from the upstream pressure source 2 can be adjusted and set so as to be adapted to the vibration transmitting unit 4. According to the control, the pressure setting valve 31.C can, for example, set the pressure over time and maintain the pressure for a specific period of time. This is convenient for certain situations. For example, when the pressure provided by the pressure source 2 may not be suitable for directly acting on the vibration transmitting unit 4 through the pressure excitation valve 33. For another example, there may be amplitude attenuation in the high vibration frequency range in the MRE technique. In this regard, manual correction is usually required in the prior art, but the real-time performance and tracking performance are poor. As a result, the signal-to-noise ratio in the high vibration frequency range is relatively poor, which increases the error in the quantitative calculation of elastic parameters of tissues and affects the accuracy of diagnosis. According to the present invention, the look-up table module 12 can set the compensation for specific elastography conditions (for example, a relatively high frequency between 60 Hz and 80 Hz). In this way, when operating under an elastography condition (for example, a high vibration frequency range) provided with compensation, the pressure setting mechanism 31 is controlled so that the pressure from the pressure source 2 is adjusted to have a compensated pressure level (for example, an increased pressure), so as to realize the correction of the amplitude and reduce the attenuation of vibration.

Preferably, the feedback logic unit 31.L is configured to receive a target input w used for the pressure setting mechanism 31 and an actual output $x_i$ from the sensor 31.s. Here, the actual output $x_i$ is a parameter sensed by the sensor 31.s of the pressure setting mechanism 31 or corresponds to same in other ways. Preferably, the feedback logic unit 31.L is configured to compare the target input w and the actual output $x_i$, so as to adjust the control of the pressure setting valve. Preferably, the pressure setting valve 31.C is a proportional hydraulic valve. The proportional hydraulic valve comprises: an inlet 31.P, which is in fluidic communication with the pressure source 2; an outlet 31.A, which is in fluidic communication with the downstream of the pressure setting valve 31.C (and preferably with the pressure excitation valve 33); a vent 31.R, which is in fluidic communication with the surrounding environment; a return spring 31.F, which is configured to press the pressure setting valve 31.C toward a preset position; and an actuator, which is used to move the valve position of the pressure setting valve 31.C. The preset position may be, for example, a valve position where the pressure setting valve 31.C is completely closed or completely open, or it may alternatively be in any valve position in between as required. Preferably, the feedback logic unit 31.L may be coupled to the actuator of the proportional relief valve so as to control its valve position.

In order to actuate the pressure setting mechanism 31 in the pressure regulating unit 3 according to the control, a control signal from the control unit 1 needs to be applied to the pressure setting mechanism 31, for example, to the feedback logic unit 31.L of the pressure setting mechanism 31. For this, the control unit 1 comprises a control module 13. The control module 13 is coupled with a look-up table module 12 and the pressure setting mechanism 31, and is configured to, based on a control parameter obtained by the look-up table module 12, generate a target input w used as the control signal for controlling the pressure setting mechanism 31. As needed, the control parameters used may involve a variety of variables coupled to the control module 13, such as the pressure, the duration of the pressure, the change curve of the pressure, etc. The target input w will limit the valve position that the pressure setting valve 31.C is in. As a result, the pressure setting valve 31.C will perform pressure setting and/or adjustment in a controlled manner.

As shown in FIG. 3, the control module 13 comprises an integrated feedback logic unit 13.L for feedback control. The integrated feedback logic unit 13.L is configured to receive a control parameter and an actual output x, and is configured to proportionally control the difference between the control parameter and the actual output x, so as to provide a regulated target input w used for the pressure setting mechanism 31. In other words, the integrated feedback logic unit 13.L is configured to perform feedback control of the pressure setting mechanism 31 based on the received actual output x. In the embodiment as shown in FIG. 3, the pressure regulating unit 3 further comprises an additional sensor s. The additional sensor s is arranged downstream of the pressure setting mechanism 31 and upstream of the pressure excitation valve 33. In this way, the actual output x is a parameter sensed by the sensor s or corresponds to same in other ways. In other embodiments not shown, the actual output x may also correspond to the actual output $x_i$ in the pressure setting mechanism 31.

For example, when the feedback control involves the actual pressure output by the pressure setting valve 31.C, the pressure setting mechanism 31 feedback-controls the pressure setting valve 31.C through the feedback logic unit 31.L, and the integrated feedback logic unit 13.L of the control module 13 compares the difference between the expected pressure and the actual pressure in order to decide whether to increase or reduce the pressure, and then the target input w after feedback adjustment will be sent to the feedback logic unit 31.L of the pressure setting mechanism 31. In the process of pressure regulation, the internal loop through the feedback logic unit 31.L of the pressure setting mechanism 31 may react faster than the external loop through the integrated feedback logic unit 13.L of the control module 13, but the external loop performs more accurate adjustments after the pressure is adjusted by the internal loop, which ensures that the output is accurately consistent with the target pressure. Here, the combination of the feedback control of the pressure setting mechanism 31 and the feedback control of the control module 13 forms a type of cascade feedback control, i.e., one that includes the internal loop of the pressure setting mechanism 31 and the external loop of the control module 13. These two loops will form a double-loop interconnection in the overall feedback loop. Conveniently, the proportional-integral-derivative (PID) control may be used for the feedback control of the pressure setting mechanism 31 and/or the feedback control of the control module 13. The cascade feedback control, preferably by PID, has good dynamic performance and is adaptive to rapidly changing working conditions. For example, the sensors s and 31.s may be pressure sensors for sensing the pressure achieved by the pressure setting valve and/or position sensors for sensing the valve position of the pressure setting valve 31.C and/or flow sensors for sensing the flow of the pressure setting valve 31.C, etc.

Thus, the control unit 1 performs automatic, accurate and repeatable continuous regulation and control of the pressure acting on the vibration transmitting unit 4 via the pressure setting mechanism 31.

Figure 4:
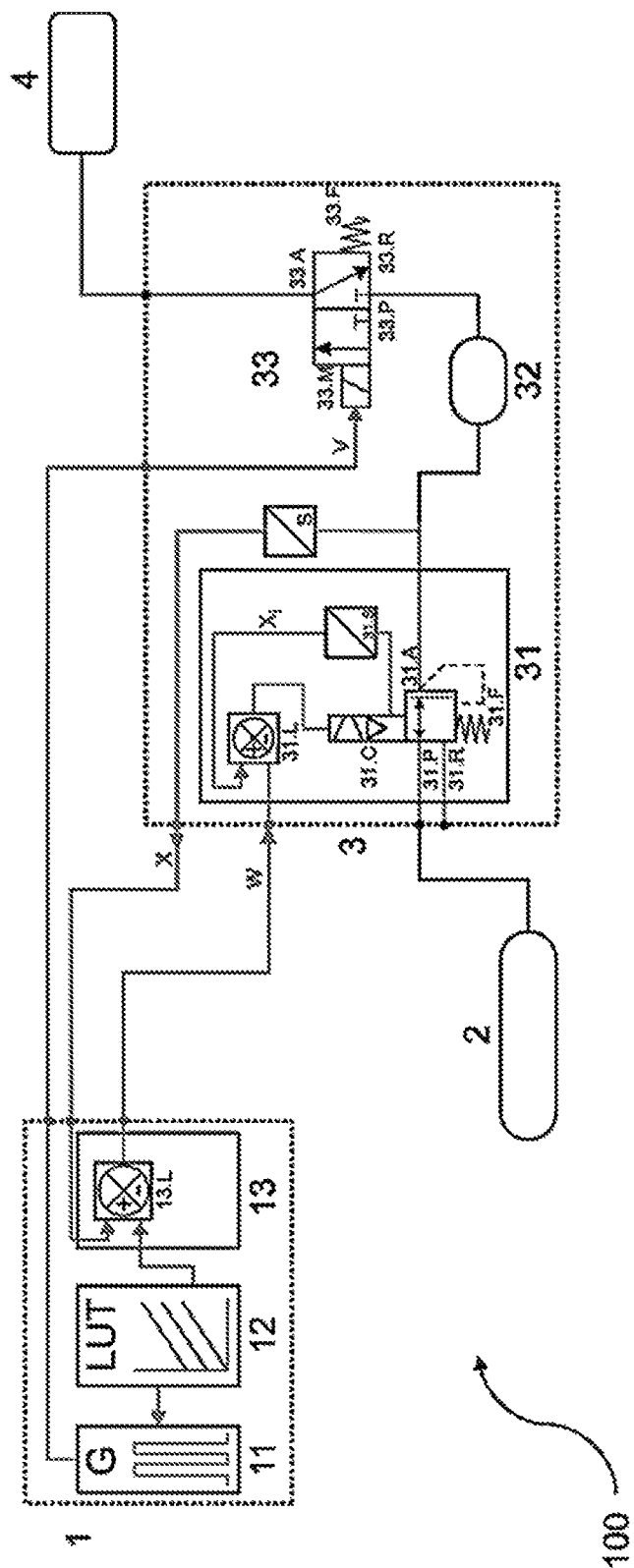
FIG. 4 shows the vibration generating system for elastography equipment according to still some embodiments of the present invention.

With reference to FIG. 4, FIG. 4 shows the vibration generating system 100 for elastography equipment according to still some other embodiments of the present invention. The embodiments of FIG. 4 are similar to those of FIGS. 1, 2 and 3.

As shown in FIG. 4, in addition to the pressure setting mechanism 31 and the pressure excitation valve 33, the pressure regulating unit 3 further comprises a pressure buffer device 32. The pressure buffer device 32 is respectively in fluidic communication with the pressure setting valve 31.C (of the pressure setting mechanism 31) and the pressure excitation valve 33. The arrangement of the pressure buffer device 32 is advantageous, because when the pressure excitation valve 33 moves between its valve positions, it may cause intermittent pressure fluctuations in the pipeline, which is not good for the accurate control of the vibration transmitting unit 4. Preferably, the pressure buffer device 32 is a small-volume air reservoir for buffering (relieving) the aforementioned pressure fluctuations. In embodiments not shown, when the pressure regulating unit 3 does not comprise the pressure setting mechanism 31, the pressure buffer device 32 may be directly connected to the pressure source 2 upstream, and it is important that the pressure fluctuations caused by the pressure excitation valve 33 (or other possible excitation parts) are buffered (relieved).

In the embodiments shown in FIGS. 1-4, the look-up table module 12 is comprised in the control unit 1. According to some other embodiments not shown, the look-up table module 12 may be comprised in the elastography equipment. Preferably, the look-up table module 12 is a look-up table that is stored in a memory and can be accessed. In this way, the memory may be the memory of the control unit 1, or alternatively, it may also be the memory of the elastography equipment or other suitable memory.

The look-up table may have the functional relation between elastography conditions and control parameters (preferably, and the pressure parameters and hence the vibration parameters). Alternatively, the look-up table may only have a discrete dataset of elastography conditions and control parameters (preferably, and the pressure parameters and hence the vibration parameters). Preferably, the corresponding control parameters (preferably, and the pressure parameters and hence the vibration parameters) have previously been determined based on optimized elastography results. That is, the look-up table module 12 has stored in it the correlation between different elastography conditions and control parameters (preferably, and the pressure parameters and hence the vibration parameters). That is, by use of the look-up table module 12, for a given elastography condition, the control parameters (preferably, and the pressure parameters and hence the vibration parameters) used for the pressure regulating unit 3 will be obtained. In the case of the abovementioned discrete dataset, the correlation that has not yet been established may be obtained by reasonable extrapolation or interpolation.

Advantageously, the look-up table is editable in order to update an existing correlation or add a new correlation. For example, another value range of an existing variable in the elastography conditions may be set, or a new variable as an elastography condition may be set.

Preferably, a user control interface may also be provided. According to some embodiments, the user control interface may be comprised in the control unit 1. According to some other embodiments, the user control interface may also be comprised in the elastography equipment. Through the user control interface, the operator may input elastography conditions for the control unit 1 to use. In addition, the operator may also make inquiries and/or edit the look-up table through the user control interface.

In the embodiments shown in FIGS. 2-4, the waveform generator 11 and the control module 13 are described as part of the control unit 1. According to some other embodiments not shown, the waveform generator 11 and/or the control module 13 may be integrated in the pressure regulating unit 3, or arranged in other ways.

The operation of the vibration generating system according to some embodiments will be described below.

According to some embodiments of the present invention, the control unit 1 receives inputted elastography conditions, uses the look-up table module 12 to obtain control parameters used for the pressure regulating unit 3 based on the inputted elastography conditions, and uses the control parameters to control the pressure regulating unit 3, and the vibration transmitting unit 4 transmits vibration according to the pressure acting thereon. As described above, the vibration will be coupled to the target tissue.

Preferably, input of elastography conditions may be done by the operator through the user control interface. In this way, the operator only needs to simply provide variables (for example, the target organ, BMI, vibration frequency, motion coding gradient, etc.) to the user control interface for use by the control unit 1. The control unit 1 will appropriately control the pressure regulating unit 3 through the look-up table module 12 according to the provided variables.

Preferably, controlling the pressure regulating unit 3 comprises controlling the pressure excitation valve 33 by use of the waveform generator 11. The pressure excitation valve 33 moves between the off position and the operating position, whereby the vibration transmitting unit 4 receives the excitation of the pressure from the pressure regulating unit 3 accordingly.

Preferably, controlling the pressure regulating unit 3 comprises controlling the pressure setting mechanism 31 by use of the control module 13. Preferably, the pressure setting mechanism performs feedback control in itself. Preferably, the control module 13 also performs feedback control on the pressure setting mechanism 31 to accurately set and regulate the pressure.

Preferably, the pressure buffer device 32 (located between the pressure excitation valve 33 and the pressure setting valve 31.C) is also used for buffering.

Although the operations of all the modules, units and/or components are described in the above order, the operations are not limited thereto. For example, they do not have to be performed in the order described above, but may be performed in other orders or even simultaneously or intertwined under appropriate circumstances.

When the vibration generating system according to the present invention is comprised in the elastography equipment, the operations include operating the vibration generating system as described above, and also include capturing an image using the elastography equipment, particularly using an image recording device.

According to still some other embodiments not shown, the vibration generating system may not comprise or use the waveform generator 11 and/or pressure excitation valve 33 as described above, but may use an arrangement in other forms. However, in some of such embodiments, the broad invention concept of the present invention may also be applied.

Two sets of elastography images are given below as comparison examples. Among them, FIG. 5 shows the elastography images of the livers of two patients under significantly different elastography conditions but the same vibration settings, and FIG. 6 shows the elastography images of the kidneys of two healthy volunteers of a similar body mass (BMI) under different vibration settings.

Figure 5:
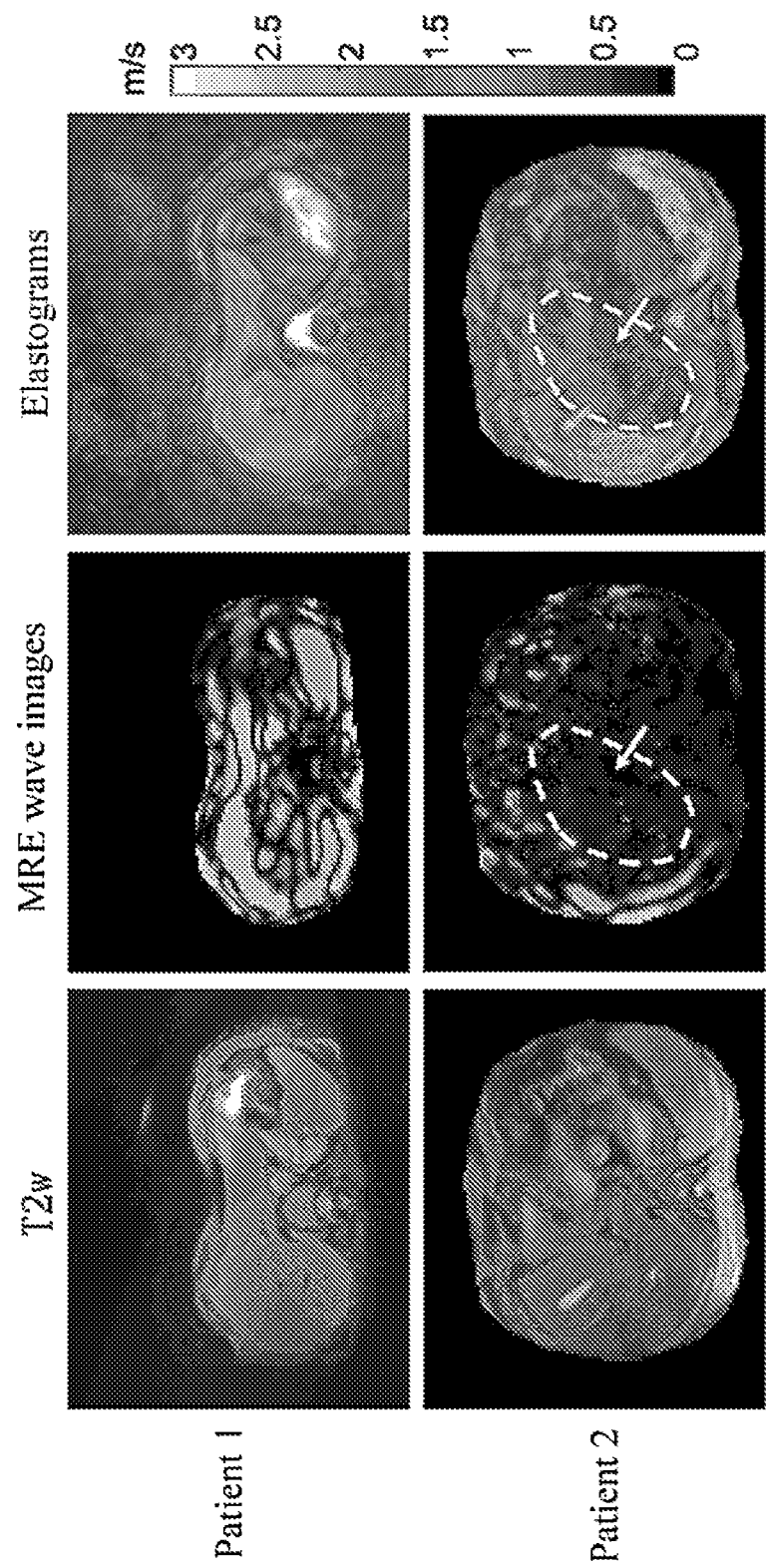
FIG. 5 shows the elastography images of the livers of two patients under significantly different elastography conditions but the same vibration settings.
Figure 6:
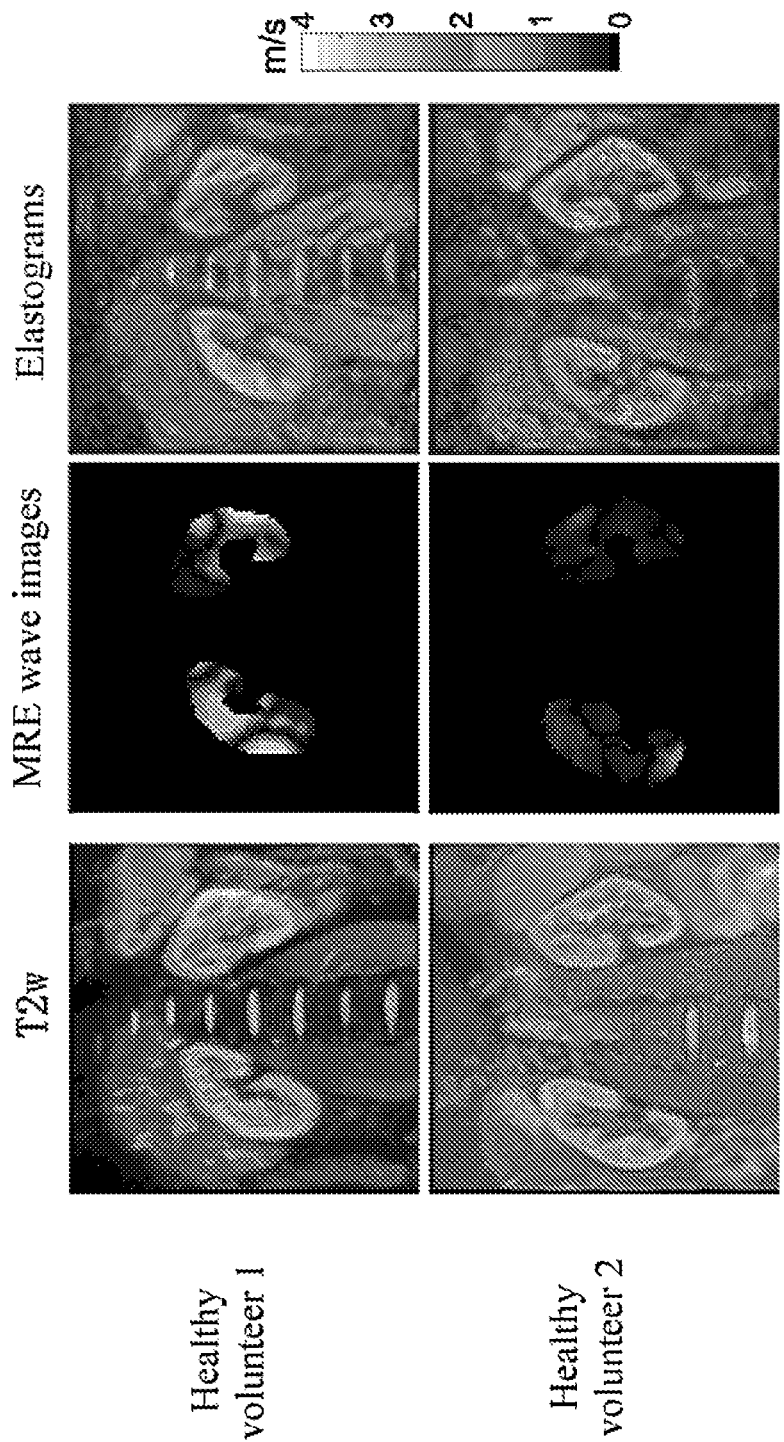
FIG. 6 shows the elastography images of the kidneys of two healthy volunteers of a similar body mass under different vibration settings.

As shown respectively in FIGS. 5 and 6, the first row shows the T2w (T2 weighted image) of MRI, the second row shows the MRE wave images, and the third row shows the elastograms.

With reference to FIG. 5, since the patients' BMIs are significantly different (a BMI of 17.3 for patient 1, and a BMI of 33.9 for patient 2), if the vibration amplitude settings (with one pre-vibration unit, at 0.2 bar, and two posterior-vibration units, at 0.3 bar) suitable for patient 1 are directly used for patient 2, vibration attenuation and insufficient penetration (in particular with reference to the area in the white dotted line with an arrow in the MRE wave images) will be caused. As a result of insufficient penetration of vibration, in the reconstructed wave images, data that may be used for analysis may be obtained only at the edges of the liver, while the true mechanical properties of the patient's liver cannot be reconstructed in areas where vibration has not penetrated (in particular with reference to the area in the white dotted line with an arrow in the elastograms).

With reference to FIG. 6, the two healthy volunteers have a similar body mass, the standard kidney MRE vibration amplitude settings (two posterior-vibration units, at 0.4 bar) are used for the elastography examination of the first healthy volunteer, and a standard elastography image is obtained, where the structures (cortex and medullar) of the kidneys are all clearly seen. Incorrect kidney MRE vibration amplitude settings (two posterior-vibration units, at 0.2 bar) are used for the elastography examination of the second healthy volunteer, the MRE wave image shows a relatively weak vibration amplitude, and the kidney structures are fuzzy in the elastogram and the reconstructed mechanical properties of the kidneys are too low, which do not conform to the standard reference value for a healthy kidney.

It can be seen that improper vibration will cause adverse impact on the MRE wave image and the elastogram.

Therefore, for example, when the vibration generating system 100 according to the present invention is used, for a first elastography condition (for example, organ: liver; status: sick; BMI: 17.3), the look-up table module 12 will have an appropriate correlated control parameter (for example, pressure settings: one anterior-vibration unit at 0.2 bar, and two posterior-vibration units at 0.3 bar). For example, when a second elastography condition is different from the first elastography condition (for example, the BMI is higher), the correlated control parameter (for example, pressure setting) in the look-up table module will be different accordingly. Similarly, for a third elastography condition (for example, organ: kidney; status: healthy; BMI: 18.5-23.9 (the common normal range)), the look-up table module 12 will have an appropriate correlated control parameter (for example, pressure setting: two posterior-vibration units at 0.4 bar). It should be noted that the terms first, second, and third used here are only to facilitate the distinction between one type of elastography condition and another type of elastography condition, and are not intended to limit it to a specific order.

In addition, the above comparison examples and the examples of the look-up table module 12 are only simple examples for illustration. In practical applications, as mentioned at the beginning, more and more complex elastography conditions that are coupled with each other will be involved. In this case, the convenient and accurate acquisition of proper vibration will be an important factor in the MRE technique. Advantageously, according to the present invention (especially in combination with the look-up table module 12), it is helpful to establish an independent standardized vibration control mechanism that does not depend on the MRI equipment and manufacturers, which is particularly suitable for multi-center studies.

The above is an explanation of the present invention, and should not be construed as a limitation to the present invention. Although some exemplary embodiments of the present invention have been described, those skilled in the art will readily understand that many modifications can be made in the exemplary embodiments without materially departing from the novelty teachings and advantages of the present invention. Therefore, all these modifications are intended to be included within the scope of the present invention as defined in the claims. The present invention is defined by the appended claims, including equivalents of the claims.

The invention claimed is:

1. A vibration generating system for elastography equipment, comprising:
a control computer comprising a control signal generator and a waveform generator:
a pressure source comprising a compressed air source;
a pressure regulating communicator;
and a vibration transducer:
wherein the pressure regulating communicator is in fluidic communication with the pressure source and vibration transducer, respectively;
wherein the vibration transducer is used to transmit vibration according to a pressure acting thereon;
wherein the control computer is coupled to the pressure regulating communicator, characterized in that the control computer is configured to obtain control parameters by using a look-up table module according to inputted elastography conditions, so as to control the pressure regulating communicator;
wherein the pressure regulating communicator comprises a pressure excitation valve and a pressure setting mechanism arranged upstream of the pressure excitation valve, the pressure setting mechanism comprising a pressure setting valve, the pressure setting valve being arranged downstream of the pressure source and in fluidic communication with the pressure source;
wherein the control signal generator is coupled to the look-up table module and the pressure setting mechanism, and is configured to generate a target input for the pressure setting mechanism on the basis of at least one of the control parameters obtained using the look-up table module, so as to control the pressure setting mechanism;
wherein the look-up table module stores correlations between various elastography conditions and control parameters for the pressure regulating communicator; and
wherein the waveform generator is coupled with the look-up table module and the pressure excitation valve, and is configured to, based on the at least one of the control parameters obtained by the look-up table module, generate a waveform signal as a control signal for controlling the pressure excitation valve.

2. The vibration generating system as claimed in claim 1, wherein the control signal generator comprises an integrated feedback logic analyzer for feedback control, the integrated feedback logic analyzer being configured to receive and analyze the at least one of the control parameters and actual output, so as to obtain an adjusted target input for the pressure setting mechanism.

3. The vibration generating system as claimed in claim 2, wherein the actual output is feedback from a sensor of the pressure setting mechanism, and/or, the actual output is feedback from an additional sensor arranged downstream of the pressure setting mechanism.

4. The vibration generating system as claimed in claim 1, wherein the-pressure regulating communicator further comprises an air reservoir.

5. The vibration generating system as claimed in claim 1, wherein the look-up table module is included in the control computer.

6. The vibration generating system as claimed in claim 1, wherein the look-up table module includes an accessible look-up table stored in a memory.

7. The vibration generating system as claimed in claim 1, wherein elastography conditions include one or more of the following: organ type, pathological state, BMI, vibration frequency, motion encoding gradient.

8. An elastography equipment comprising a Magnetic Resonance Imaging (MRI) system and the vibration generating system as claimed in claim 1.

9. A method for controlling a vibration generating system for elastography equipment, wherein the vibration generating system comprises a control computer having a control signal generator and a waveform generator, a pressure source comprising a compressed air source, a pressure regulating communicator, and a vibration transducer, wherein the-pressure regulating communicator is in fluidic communication with the pressure source and the vibration transducer, respectively, said pressure regulating communicator comprises a pressure excitation valve and a pressure setting mechanism arranged upstream of the pressure excitation valve, the pressure setting mechanism, having a pressure setting valve, where the pressure setting valve is arranged downstream of the pressure source and in fluidic communication with the pressure source, the method comprising:
- obtaining control parameters, via the control computer by using a look-up table module, according to inputted elastography conditions to control the pressure regulating communicator;
- generating a target input, via the control signal generator coupled to the look-up table module and the pressure setting mechanism, for the pressure setting mechanism on the basis of at least one of the control parameters obtained using the look-up table module to control the pressure setting mechanism;
- storing correlations between various elastography conditions and control parameters for the pressure regulating communicator in the look-up table module;
- generating a wave form signal as the control signal for controlling the pressure excitation valve, via the wave form generator coupled with the look-up table module and pressure excitation valve, based on the at least one of the control parameters obtained by the look-up table module.

10. The method as claimed in claim 9, wherein the control signal generator further receives an actual output from the pressure setting mechanism and/or another sensor, and uses the actual output for feedback control.

11. The method as claimed in claim 10, wherein proportional-integral-derivative control and/or cascade feedback control is adopted as the feedback control.

12. The method as claimed in claim 9, further comprising using an air reservoir for buffering.

13. A method for operating elastography equipment, comprising: inputting elastography conditions; controlling a vibration generating system by using the method as claimed in claim 7; and acquiring an image by using a Magnetic Resonance Imaging (MRI) system.

14. A physical and nonvolatile computer-readable medium storing a look-up table that contains correlations between elastography conditions and control parameters of a vibration generating system comprising a control computer having a waveform generator and a control signal generator,
- a pressure source having a compressed air source,
- a pressure regulating communicator having a pressure excitation valve and pressure setting mechanism arranged upstream of the pressure excitation valve, the pressure setting mechanism comprising a pressure setting valve arranged downstream of the pressure source, and a vibration transducer in fluidic communication with the pressure regulating communicator;
- wherein a computer instruction stored in the computer-readable medium or another computer instruction, when executed by a processor, is configured to:
- obtain the control parameters, via the control computer by using the look-up table, according to inputted elastography conditions to control the pressure regulating communicator;
- generate a target input, via the control signal generator coupled to the look-up table and the pressure setting mechanism, for the pressure setting mechanism on the basis of at least one of the control parameters obtained using the look-up table to control the pressure setting mechanism;
- store correlations between various elastography conditions and control parameters for the pressure regulating communicator in the look-up table;
- generate a wave form signal as a control signal for controlling the pressure excitation valve, via a wave form generator coupled with the look-up table and the pressure excitation valve, based on the at least one of the control parameters obtained by the look-up table.

* * * * *